US012673185B2

(12) United States Patent
Hartley et al.

(10) Patent No.: US 12,673,185 B2
(45) Date of Patent: Jul. 7, 2026

(54) INTEGRATED CATHETER-PLACEMENT DEVICES AND METHODS FOR MITIGATING BLOOD EGRESS

(71) Applicant: Bard Access Systems, Inc., Salt Lake City, UT (US)

(72) Inventors: Lori L. Hartley, Salt Lake City, UT (US); Glade H. Howell, Draper, UT (US); Eric W. Lindekugel, Salt Lake City, UT (US); Bradley J. VanderStek, West Bountiful, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 965 days.

(21) Appl. No.: 17/381,809

(22) Filed: Jul. 21, 2021

(65) Prior Publication Data

US 2022/0023598 A1     Jan. 27, 2022

Related U.S. Application Data

(60) Provisional application No. 63/055,103, filed on Jul. 22, 2020.

(51) Int. Cl.
   *A61M 25/06*     (2006.01)
   *A61M 25/00*     (2006.01)
   *A61M 25/09*     (2006.01)

(52) U.S. Cl.
   CPC .... *A61M 25/0693* (2013.01); *A61M 25/0097* (2013.01); *A61M 25/0606* (2013.01);
   (Continued)

(58) Field of Classification Search
   CPC .......... A61M 25/0097; A61M 25/0606; A61M 25/09041; A61M 25/09; A61M 25/065;
   (Continued)

(56) References Cited

U.S. PATENT DOCUMENTS

| | | |
|---|---|---|
| 3,728,035 A | 4/1973 | Reitknecht et al. |
| 8,690,833 B2 | 4/2014 | Belson |
| | (Continued) | |

OTHER PUBLICATIONS

PCT/US2021/042557 filed Jul. 21, 2021 International Search Report and Written Opinion dated Nov. 24, 2021.

*Primary Examiner* — Michael J Tsai
*Assistant Examiner* — Kathleen Paige Farrell
(74) *Attorney, Agent, or Firm* — Rutan & Tucker LLP

(57) ABSTRACT

Disclosed herein are integrated catheter-placement devices and methods thereof. An exemplary device includes an intravascular catheter, a needle, an access guidewire, and a blood egress-mitigating means for mitigating blood egress from the device. The intravascular catheter includes a catheter tube and catheter hub. The catheter extends from a body of the device. The needle includes a needle shaft and a needle hub. The needle shaft extends through the catheter tube by way of a catheter-tube lumen thereof. The access guidewire is disposed in a needle lumen of the needle. The blood egress-mitigating means mitigates blood egress from the device by mitigating blood egress from an annular space within the needle shaft while still allowing the access guidewire to axially move within the needle lumen. The annular space is defined by a luminal surface of the needle shaft and a surface of the access guidewire.

17 Claims, 11 Drawing Sheets

DISTAL                                                    PROXIMAL

(52) U.S. Cl.
CPC .................. *A61M 25/09041* (2013.01); *A61M 2205/0222* (2013.01)

(58) Field of Classification Search
CPC .............. A61M 25/01; A61M 25/0693; A61M 2205/0222; A61M 2025/09133; A61M 25/0631; A61M 25/0618; A61M 5/158; A61M 2039/062; A61M 25/0637; A61B 17/3415; A61B 17/3421; A61B 5/15003; A61B 5/150389; A61B 5/150992; A61B 5/1535; A61B 5/1545; A61B 5/153
See application file for complete search history.

(56) References Cited

U.S. PATENT DOCUMENTS

| | | | |
|---|---|---|---|
| 8,721,546 | B2 | 5/2014 | Belson |
| 8,932,258 | B2 | 1/2015 | Blanchard et al. |
| 8,986,227 | B2 | 3/2015 | Belson |
| 8,998,852 | B2 | 4/2015 | Blanchard et al. |
| D733,289 | S | 6/2015 | Blanchard et al. |
| D735,321 | S | 7/2015 | Blanchard |
| 9,095,683 | B2 | 8/2015 | Hall et al. |
| 9,162,037 | B2 | 10/2015 | Belson et al. |
| 9,522,254 | B2 | 12/2016 | Belson |
| 9,616,201 | B2 | 4/2017 | Belson |
| 9,675,784 | B2 | 6/2017 | Belson |
| 9,757,540 | B2 | 9/2017 | Belson |
| 9,861,792 | B2 | 1/2018 | Hall et al. |
| 9,872,971 | B2 | 1/2018 | Blanchard |
| 9,950,139 | B2 | 4/2018 | Blanchard et al. |
| 10,086,171 | B2 | 10/2018 | Belson |
| 10,220,191 | B2 | 3/2019 | Belson et al. |
| 10,232,146 | B2 | 3/2019 | Braithwaite et al. |
| 10,265,507 | B2 | 4/2019 | Belson |
| 10,328,239 | B2 | 6/2019 | Belson |
| 10,384,039 | B2 | 8/2019 | Ribelin et al. |
| 10,426,931 | B2 | 10/2019 | Blanchard et al. |
| 10,493,262 | B2 | 12/2019 | Tran et al. |
| 10,525,236 | B2 | 1/2020 | Belson |
| 10,688,280 | B2 | 6/2020 | Blanchard et al. |
| 10,688,281 | B2 | 6/2020 | Blanchard et al. |
| 10,722,685 | B2 | 7/2020 | Blanchard et al. |
| 10,799,680 | B2 | 10/2020 | Belson |
| 10,806,906 | B2 | 10/2020 | Warring et al. |
| D903,100 | S | 11/2020 | Stats et al. |
| D903,101 | S | 11/2020 | Stats et al. |
| 10,912,930 | B2 | 2/2021 | Warring et al. |
| 11,000,678 | B2 | 5/2021 | Hall |
| D921,884 | S | 6/2021 | Tran et al. |
| 11,020,571 | B2 | 6/2021 | Belson et al. |
| 11,033,719 | B2 | 6/2021 | Braithwaite |
| 11,040,176 | B2 | 6/2021 | Blanchard et al. |
| 11,123,524 | B2 | 9/2021 | Hall et al. |
| 11,135,406 | B2 | 10/2021 | Ribelin et al. |
| 11,202,886 | B2 | 12/2021 | Belson |
| 11,278,702 | B2 | 3/2022 | Blanchard |

| | | | |
|---|---|---|---|
| 2006/0240253 | A1* | 10/2006 | Bavaro et al. ............................... A61M 2025/09133 |
| 2008/0300574 | A1 | 12/2008 | Belson et al. |
| 2009/0221961 | A1* | 9/2009 | Tal et al. ........... A61M 25/0606 |
| 2010/0094310 | A1 | 4/2010 | Warring et al. |
| 2010/0210934 | A1 | 8/2010 | Belson |
| 2011/0282285 | A1 | 11/2011 | Blanchard et al. |
| 2012/0197200 | A1 | 8/2012 | Belson |
| 2012/0220942 | A1 | 8/2012 | Hall et al. |
| 2014/0031752 | A1 | 1/2014 | Blanchard et al. |
| 2014/0094774 | A1 | 4/2014 | Blanchard |
| 2014/0180250 | A1 | 6/2014 | Belson |
| 2014/0188003 | A1 | 7/2014 | Belson |
| 2014/0214005 | A1 | 7/2014 | Belson |
| 2014/0378867 | A1 | 12/2014 | Belson |
| 2015/0038943 | A1 | 2/2015 | Warring et al. |
| 2015/0119806 | A1 | 4/2015 | Blanchard et al. |
| 2015/0231364 | A1 | 8/2015 | Blanchard et al. |
| 2015/0290431 | A1 | 10/2015 | Hall et al. |
| 2016/0015943 | A1 | 1/2016 | Belson et al. |
| 2016/0015945 | A1 | 1/2016 | Warring et al. |
| 2016/0022963 | A1 | 1/2016 | Belson |
| 2016/0045715 | A1* | 2/2016 | Galgano et al. .. A61M 25/0606 |
| 2016/0067453 | A1* | 3/2016 | Braithwaite et al. ........................ A61M 25/0606 |
| 2016/0121086 | A1 | 5/2016 | Castro et al. |
| 2016/0256667 | A1 | 9/2016 | Ribelin et al. |
| 2016/0331938 | A1 | 11/2016 | Blanchard et al. |
| 2017/0087338 | A1 | 3/2017 | Belson |
| 2017/0209668 | A1 | 7/2017 | Belson |
| 2017/0259036 | A1 | 9/2017 | Belson |
| 2017/0361071 | A1 | 12/2017 | Belson |
| 2018/0028780 | A1 | 2/2018 | Blanchard et al. |
| 2018/0071509 | A1 | 3/2018 | Tran et al. |
| 2018/0092651 | A1* | 4/2018 | Terashi et al. ........ A61M 25/09 |
| 2018/0126125 | A1 | 5/2018 | Hall et al. |
| 2018/0133437 | A1 | 5/2018 | Blanchard |
| 2018/0229003 | A1 | 8/2018 | Blanchard et al. |
| 2018/0229004 | A1 | 8/2018 | Blanchard et al. |
| 2019/0022358 | A1 | 1/2019 | Belson |
| 2019/0192829 | A1 | 6/2019 | Belson et al. |
| 2019/0201667 | A1 | 7/2019 | Braithwaite et al. |
| 2019/0240459 | A1 | 8/2019 | Belson |
| 2019/0275303 | A1 | 9/2019 | Tran et al. |
| 2019/0307986 | A1 | 10/2019 | Belson |
| 2019/0351193 | A1 | 11/2019 | Hall |
| 2019/0351196 | A1 | 11/2019 | Ribelin et al. |
| 2020/0001051 | A1 | 1/2020 | Huang et al. |
| 2020/0094037 | A1 | 3/2020 | Tran et al. |
| 2020/0261696 | A1 | 8/2020 | Blanchard |
| 2020/0261703 | A1 | 8/2020 | Belson et al. |
| 2020/0316347 | A1 | 10/2020 | Belson |
| 2021/0052858 | A1 | 2/2021 | Isaacson et al. |
| 2021/0154441 | A1 | 5/2021 | Warring et al. |
| 2021/0283379 | A1 | 9/2021 | Hadley et al. |
| 2021/0308428 | A1 | 10/2021 | Blanchard et al. |
| 2021/0402155 | A1 | 12/2021 | Hall et al. |
| 2022/0062596 | A1 | 3/2022 | Ribelin et al. |

* cited by examiner

PROXIMAL

DISTAL

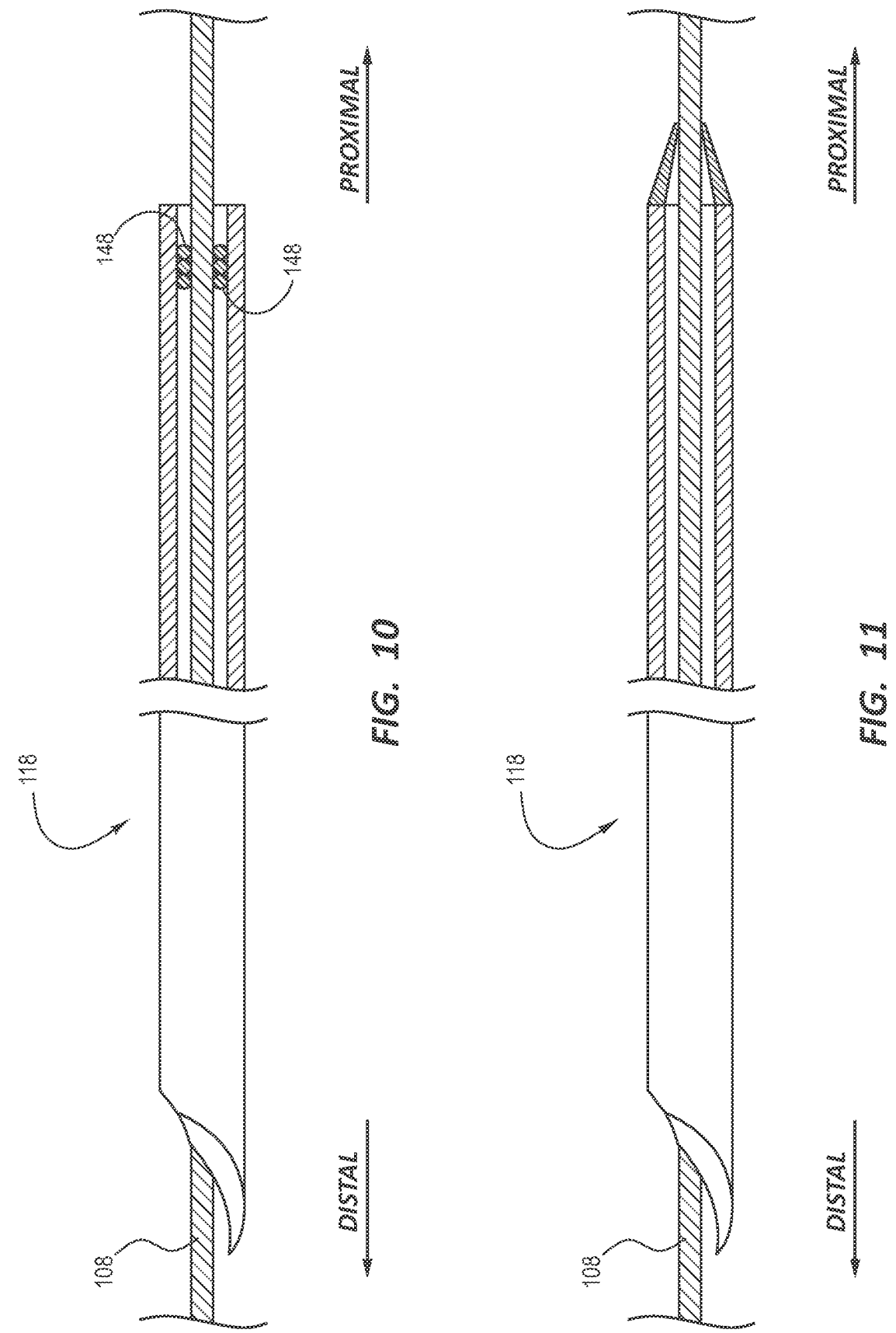

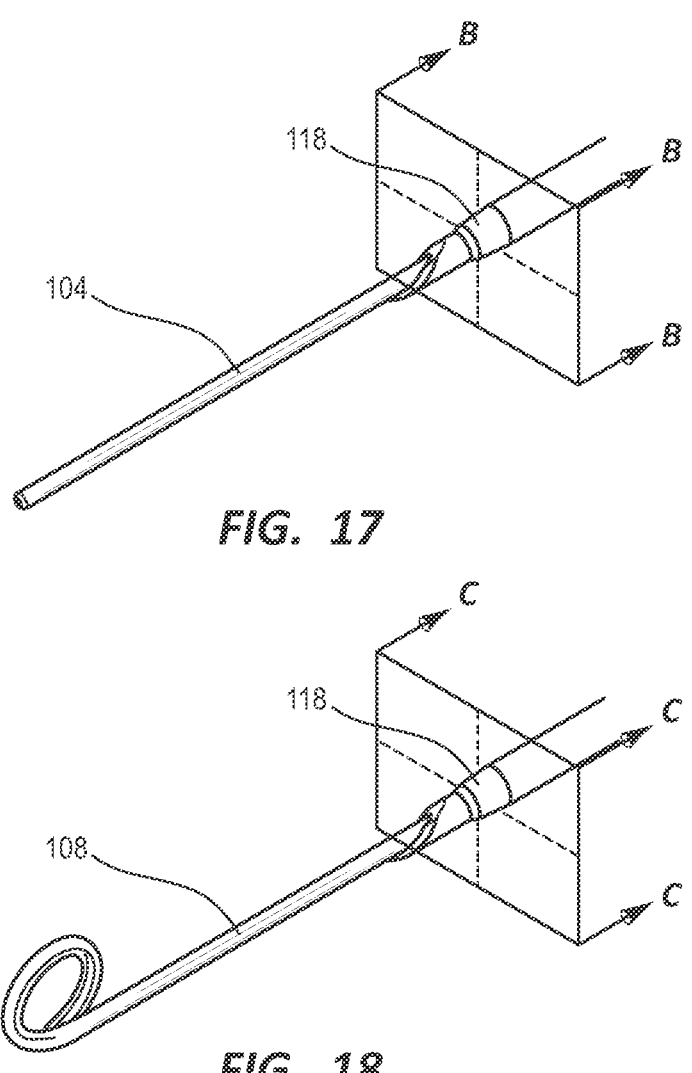
FIG. 17
FIG. 18
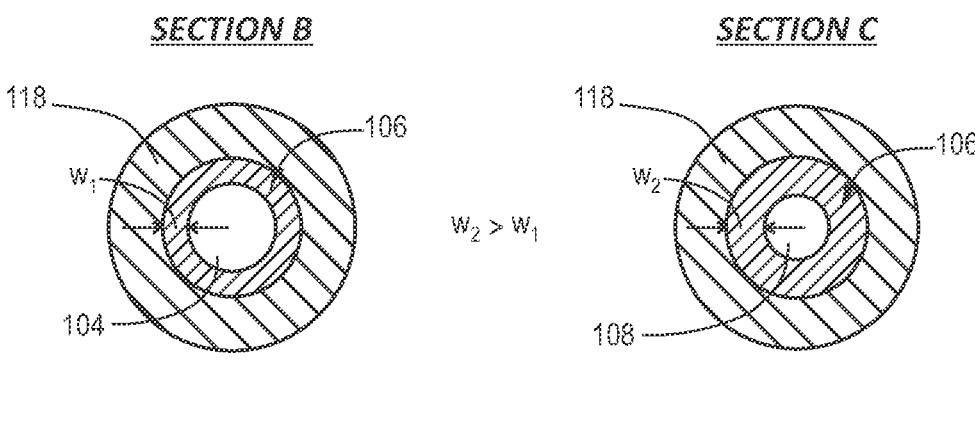
SECTION B
SECTION C
$w_2 > w_1$
FIG. 19          FIG. 20

INTEGRATED CATHETER-PLACEMENT DEVICES AND METHODS FOR MITIGATING BLOOD EGRESS

PRIORITY

This application claims priority to U.S. Provisional Application No. 63/055,103, filed Jul. 22, 2020, which is incorporated by reference in its entirety into this application.

BACKGROUND

Integrated catheter-placement devices such as the Pow-erGlide PRO™ midline catheter, the AccuCath™ intravascular catheter, and the AccuCath Ace™ intravascular catheter by Becton, Dickinson, and Company ("BD") of Franklin Lakes, N.J., provide all-in-one solutions for quickly placing intravascular catheters and gaining peripheral vascular access. Such catheters are subject to International Organization for Standardization ("ISO") standards such as ISO 10555-5, which specifies requirements for over-needle peripheral intravascular catheters.

As shown among FIGS. 1A, 1B, and 17, an integrated catheter-placement device 100 such as the PowerGlide PRO™ midline catheter includes a needle 102 for establishing a needle tract to a blood-vessel lumen and an access guidewire 104 (e.g., a wound access guidewire) disposed in the needle 102 for immediately advancing the access guidewire 104 into the blood-vessel lumen upon establishing access thereto. As shown in FIG. 19, an annular space 106 between a luminal surface of the needle 102 and a surface of the access guidewire 104 allows blood to flash back into the device 100, which is a useful indicator of access to the blood-vessel lumen; however, the blood resulting from the flashback must be contained within the device 100 for a specified period of time at a specified pressure without egress in accordance with ISO 10555-5. This presents challenges in manufacturing when, out of want or need, sourcing for a component changes such as from the access guidewire 104 to another access guidewire 108 (e.g., the bare, non-wound AccuTip™ guidewire by BD). (See FIGS. 1A, 1B, and 18.) Changes in sourcing can, in turn, bring about changes in tolerances such as that of the annular space 106 as shown between FIGS. 19 and 20, wherein an annular width w₂ of the annular space 106 is greater than an annular width w₁ of the annular space 106 when the access guidewire 104 is replaced with the access guidewire 108. Changes in tolerances, can, in turn, move an integrated catheter-placement device out of compliance with respect to, for example, blood egress from the needle 102 under ISO 10555-5 if the annular space 106 is increased.

Disclosed herein are integrated catheter-placement devices and methods thereof that address the foregoing.

SUMMARY

Disclosed herein is an integrated catheter-placement device including an intravascular catheter, a needle, an access guidewire, and a blood egress-mitigating means for mitigating blood egress from the device. The intravascular catheter includes a catheter tube and catheter hub. The catheter extends from a body of the device in at least a ready-to-deploy state of the device. The needle includes a needle shaft and a needle hub. The needle shaft extends through the catheter tube by way of a catheter-tube lumen thereof in at least the ready-to-deploy state of the device. The access guidewire is disposed in a needle lumen of the needle. The blood egress-mitigating means mitigates blood egress from the device by mitigating blood egress from an annular space within the needle shaft while still allowing the access guidewire to axially move within the needle lumen. The annular space is defined by a luminal surface of the needle shaft and a surface of the access guidewire.

In some embodiments, the blood egress-mitigating means includes a swaged or crimped section in a proximal portion of the needle shaft having a smaller outer diameter than a remainder of the needle shaft. The swaged or crimped section has a reduced annular space for retarding blood flow therethrough.

In some embodiments, the needle hub is disposed over the swaged or crimped section of the needle shaft and coupled thereto.

In some embodiments, a transverse cross section of the reduced annular space in the swaged or crimped section of the needle shaft has a minimum annular width of about 25 µm.

In some embodiments, the blood egress-mitigating means includes an embossed section in a proximal portion of the needle shaft having a plurality of embossments in an abluminal surface of the needle shaft extending into the annular space. The plurality of embossments in the embossed section contributes to a reduced annular space for retarding blood flow through the embossed section.

In some embodiments, the plurality of embossments in the embossed section provide a torturous fluid path for the blood flow therethrough.

In some embodiments, the blood egress-mitigating means includes a reservoir in a proximal portion of the needle shaft. The reservoir provides a space for collecting blood therein.

In some embodiments, the reservoir is integral with the needle shaft. The proximal portion of the needle shaft terminates with the reservoir.

In some embodiments, the reservoir is a container disposed over a proximal end of the needle shaft.

In some embodiments, the reservoir includes a guidewire aperture in a proximal end thereof through which the access guidewire is allowed to axially move.

In some embodiments, the reservoir is disposed between proximal and distal members of the needle hub.

In some embodiments, the reservoir is disposed in the integrated catheter-placement device proximal of a proximal member of the needle hub.

In some embodiments, the blood egress-mitigating means further includes a superabsorbent polymer, a cellulosic polymer, a coagulant, or a combination thereof disposed in the reservoir. Optionally, the superabsorbent polymer, a cellulosic polymer, the coagulant, or the combination thereof is dispersed or dissolved in a liquid.

In some embodiments, the blood egress-mitigating means includes a tubular insert inserted into a proximal portion of the needle shaft between the needle shaft and the access guidewire. The tubular insert assumes a portion of the needle lumen. By assuming a portion of the needle lumen, the tubular insert contributes to a reduced annular space for retarding blood flow through the needle lumen.

In some embodiments, the tubular insert is porous with a porosity configured to allow air but not blood therethrough.

In some embodiments, the blood egress-mitigating means includes a holed stopper inserted into a proximal end of the needle shaft. A distal portion of the holed stopper assumes a portion of the needle lumen in a proximal portion of the needle shaft. By assuming a portion of the needle lumen, the holed stopper contributes to a reduced annular space for retarding blood flow through the needle lumen.

In some embodiments, the holed stopper includes a longitudinal through hole through which the access guidewire is allowed to axially move.

In some embodiments, the holed stopper is porous with a porosity configured to allow air but not blood therethrough.

In some embodiments, the blood egress-mitigating means includes one or more 'O'-rings inserted into a proximal portion of the needle shaft between the needle shaft and the access guidewire. The one-or-more 'O'-rings assume a portion of the needle lumen. By assuming a portion of the needle lumen, the one-or-more 'O'-rings contribute to a reduced annular space for retarding blood flow through the needle lumen.

In some embodiments, the blood egress-mitigating means includes a conical funnel having a mouth coupled to a proximal end of the needle shaft. The conical funnel proximally tapers onto the access guidewire, which retards blood flow through a proximal opening of the conical funnel.

In some embodiments, the blood egress-mitigating means includes a bore through a distal face of a proximal member of the needle hub having a through hole dimensioned such that only the access guidewire is allowed therethrough. By allowing only the access guidewire through the through hole, the through hole contributes to a reduced annular space for retarding blood flow through a proximal end of the needle shaft.

In some embodiments, the blood egress-mitigating means includes a superabsorbent polymer, a cellulosic polymer, a coagulant, or a combination thereof disposed in the needle lumen in a proximal end of the needle shaft. Optionally, the superabsorbent polymer, a cellulosic polymer, the coagulant, or the combination thereof is dispersed or dissolved in a liquid.

In some embodiments, the blood egress-mitigating means includes an amount of an oil-based lubricant disposed in the needle lumen in a proximal portion of the needle shaft. The lubricant blocks or retards blood flow through a proximal end of the needle shaft.

In some embodiments, the needle shaft includes a cutout through a needle-shaft wall in the proximal portion of the needle shaft. The cutout is configured for injecting the lubricant into the needle lumen.

In some embodiments, the blood egress-mitigating means includes a superabsorbent polymer, a cellulosic polymer, a coagulant, or a combination thereof disposed on the surface of the access guidewire. Optionally, the superabsorbent polymer, a cellulosic polymer, the coagulant, or the combination thereof is dispersed or dissolved in a liquid.

In some embodiments, the blood egress-mitigating means includes a polymeric coating over the surface of the access guidewire. The polymeric coating assumes a portion of the needle lumen. By assuming a portion of the needle lumen, the polymeric coating contributes to a reduced annular space for retarding blood flow through the needle lumen.

Also disclosed herein is a method of an integrated catheter-placement device. The method includes an obtaining step, a needle tract-establishing step, an access guidewire-advancing step, a catheter-advancing step, and a withdrawing step. The obtaining step includes obtaining the device. The device includes a needle including a needle shaft disposed in a catheter tube of an intravascular catheter in at least a ready-to-deploy state of the device. The needle tract-establishing step includes establishing a needle tract from an area of skin to a blood-vessel lumen of a patient with the needle. The needle tract-establishing step causes blood to flash back into the device but without egressing from the device in accordance with a blood egress-mitigating means for mitigating blood egress from the device. The access guidewire-advancing step includes advancing an access guidewire disposed in a needle lumen of the needle into the blood-vessel lumen. The catheter-advancing step includes advancing the catheter tube over the needle and into the blood-vessel lumen. The withdrawing step includes withdrawing both the needle and the access guidewire from the blood-vessel lumen leaving the catheter behind with the catheter tube disposed in the blood-vessel lumen of the patient.

In some embodiments, the blood egress-mitigating means reduces or blocks an annular space within the needle shaft defined by a luminal surface of the needle shaft and a surface of the access guidewire for retarding or blocking blood flow therethrough.

In some embodiments, the blood egress-mitigating means includes a reservoir fluidly coupled to the needle lumen for collecting blood therein.

In some embodiments, the blood egress-mitigating means includes a composition including a superabsorbent polymer, a cellulosic polymer, a coagulant, or a combination thereof for absorbing or coagulating blood therewith.

These and other features of the concepts provided herein will become more apparent to those of skill in the art in view of the accompanying drawings and following description, which describe particular embodiments of such concepts in greater detail.

DRAWINGS

FIG. 10 illustrates one or more 'O'-rings inserted into the needle shaft in accordance with some embodiments.

FIG. 11 illustrates a conical funnel coupled to the needle shaft in accordance with some embodiments.

FIG. 17 illustrates a distal portion of an integrated catheter-placement device with a first access guidewire disposed in a needle shaft in accordance with some embodiments.

FIG. 18 illustrates the distal portion of the integrated catheter-placement device with a second access guidewire disposed in the needle shaft in accordance with some embodiments.

FIG. 19 illustrates a transverse cross section of the first access guidewire disposed in the needle shaft in accordance with some embodiments.

FIG. 20 illustrates a transverse cross section of the second access guidewire disposed in the needle shaft in accordance with some embodiments.

DESCRIPTION

Figure 1A:
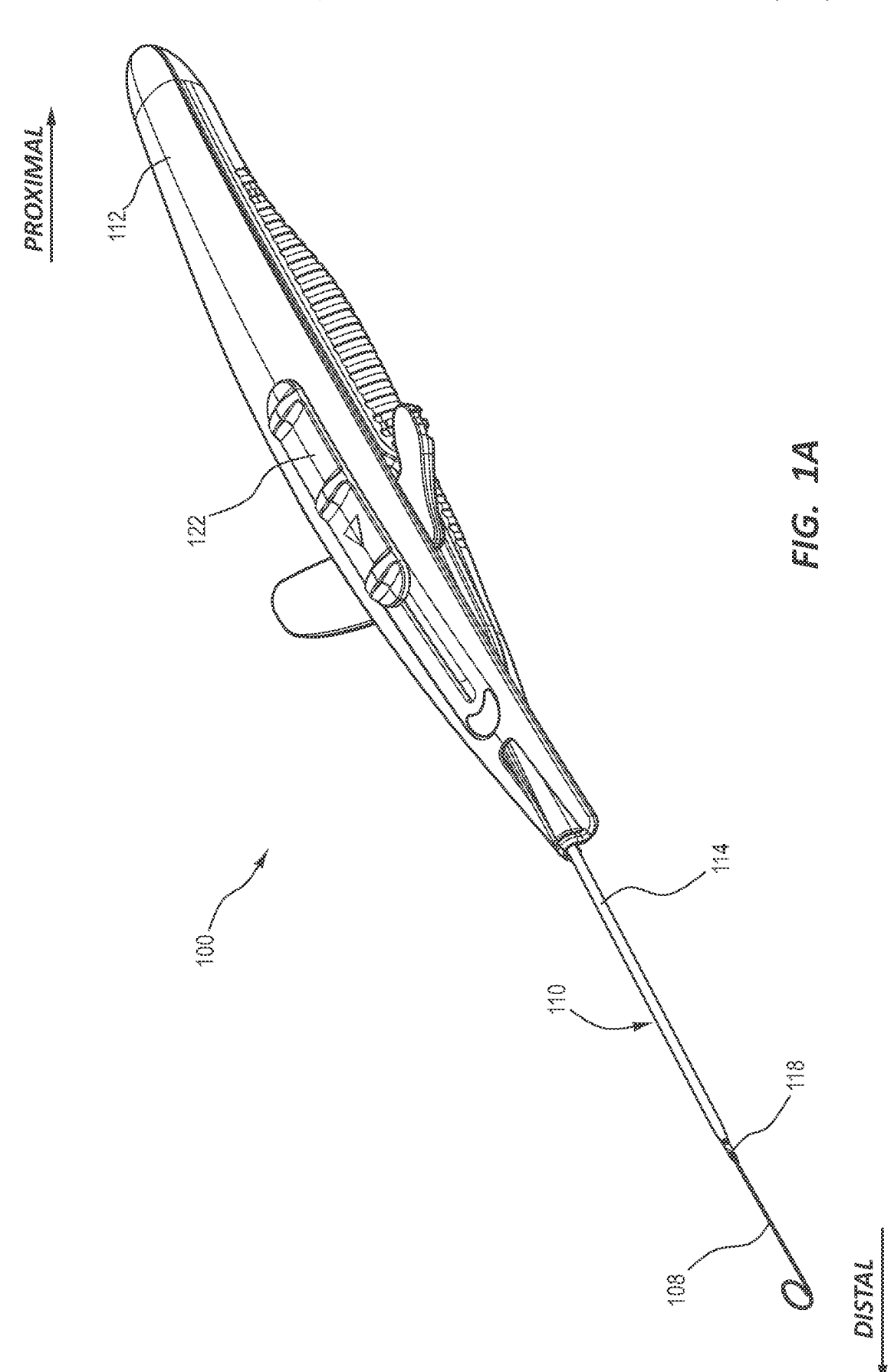
FIG. 1A illustrates an isometric view of an integrated catheter-placement device in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal-end portion, or the proximal length of the catheter can include the proximal end of the catheter; however, the proximal portion, the proximal-end portion, or the proximal length of the catheter need not include the proximal end of the catheter. That is, unless context suggests otherwise, the proximal portion, the proximal-end portion, or the proximal length of the catheter is not a terminal portion or terminal length of the catheter.

With respect to "distal," a "distal portion" or a "distal-end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal-end portion, or the distal length of the catheter can include the distal end of the catheter; however, the distal portion, the distal-end portion, or the distal length of the catheter need not include the distal end of the catheter. That is, unless context suggests otherwise, the distal portion, the distal-end portion, or the distal length of the catheter is not a terminal portion or terminal length of the catheter.

Unless defined otherwise, all technical and scientific terms used herein have the same meaning as commonly understood by those of ordinary skill in the art.

As set forth above, changes in sourcing for a component such as the access guidewire 104 can bring about changes in tolerances such as that of the annular space 106 as shown between FIGS. 19 and 20, wherein the annular width $w_2$ of the annular space 106 is greater than the annular width $w_1$ of the annular space 106 when the access guidewire 104 is replaced with the access guidewire 108. Changes in tolerances, can, in turn, move an integrated catheter-placement device out of compliance with respect to, for example, blood egress from the needle 102 under ISO 10555-5 if the annular space 106 is increased.

Disclosed herein are integrated catheter-placement devices and methods thereof that address the foregoing. However, it should be understood that the devices and methods set forth below need not be dependent upon changes in sourcing or the like. Indeed, the concepts provided herein can be implemented into any integrated catheter-placement device or the like for complying with ISO 10555-5 or otherwise.

Integrated Catheter-Placement Devices

Figure 1B:
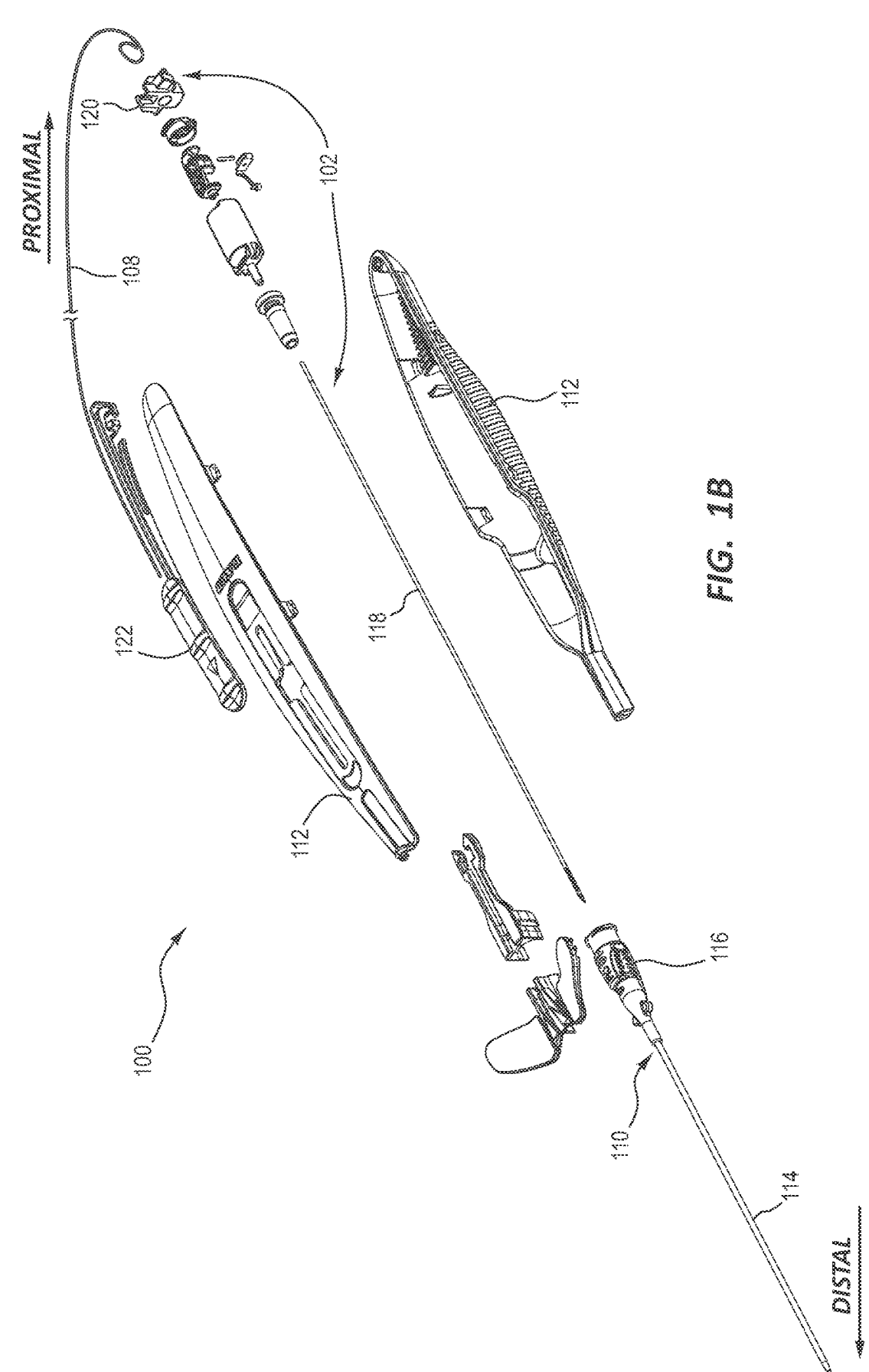
FIG. 1B illustrates an exploded view of the integrated catheter-placement device in accordance with some embodiments.

FIGS. 1A and 1B illustrate different views of the integrated catheter-placement device 100 in accordance with some embodiments.

As shown, the device 100 includes an intravascular catheter 110, the needle 102, and the access guidewire 108 disposed in a body 112 of the device 100 in at least a ready-to-deploy state of the device 100. The device 100 also includes a blood egress-mitigating means for mitigating blood egress from the device 100 in at least an operating state of the device 100. The blood egress-mitigating means is set forth below in a number of embodiments.

The catheter 110 includes a catheter tube 114 and catheter hub 116. The catheter 110 extends from the body 112 of the device 100 in at least the ready-to-deploy state of the device 100. The catheter 110 is configured to decouple from the device 100 for leaving the catheter 110 in place in a blood-lumen vessel of a patient.

Figure 2:
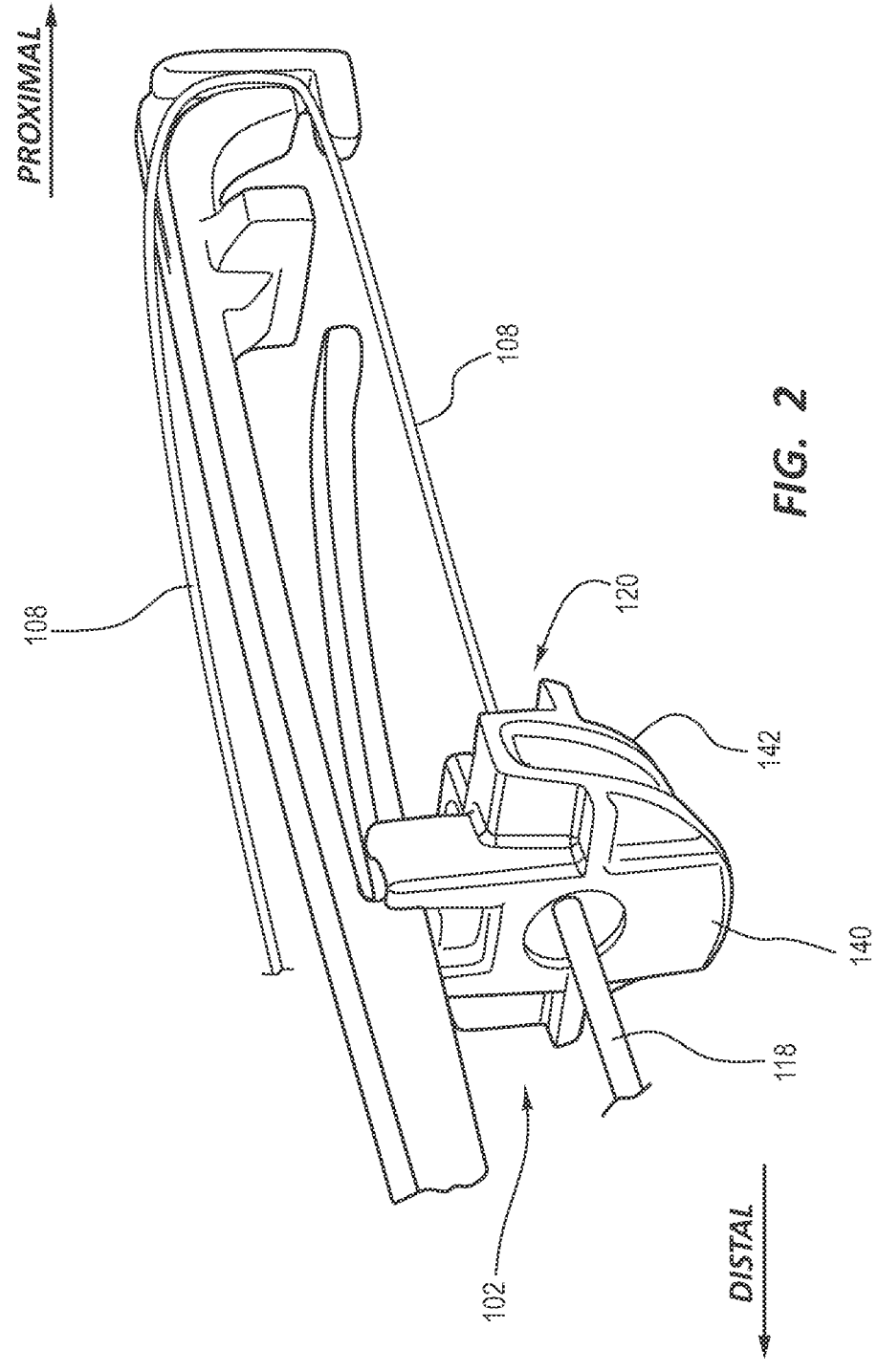
FIG. 2 illustrates a close-up view of a needle shaft disposed in a needle hub of the integrated catheter-placement device in accordance with some embodiments.

FIG. 2 illustrates a close-up view of a needle shaft 118 disposed in a needle hub 120 of the device 100 in accordance with some embodiments.

As shown, the needle 102 includes the needle shaft 118 and the needle hub 120. The needle shaft 118 extends through the catheter tube 114 by way of a catheter-tube lumen thereof in at least the ready-to-deploy state of the device 100. The needle 102 is configured to establish a needle tract to a blood-vessel lumen of a patient for deploying the catheter 110.

The access guidewire 108 is disposed in a needle lumen of the needle 102. (See FIG. 20 for the access guidewire 108 in the needle lumen.) The access guidewire 108 is configured for guiding advancement of the catheter 110 over the needle 102 and into a blood-vessel lumen.

Other components of the device 100 are set forth in at least U.S. Pat. No. 9,950,139, the disclosure of which is incorporated into this application in its entirety.

The blood egress-mitigating means mitigates blood egress from the device 100 by mitigating blood egress from the annular space 106 within the needle shaft 118 while still allowing the access guidewire 108 to axially move within the needle lumen when advanced by a slider 122 atop the body 112 of the device 100. Again, the annular space 106 is defined by the luminal surface of the needle 102, particularly that of the needle shaft 118, and the surface of the access guidewire 108.

Needle Modifications: Swaged or Crimped Sections of the Needle Shaft

Figures 3, 4:
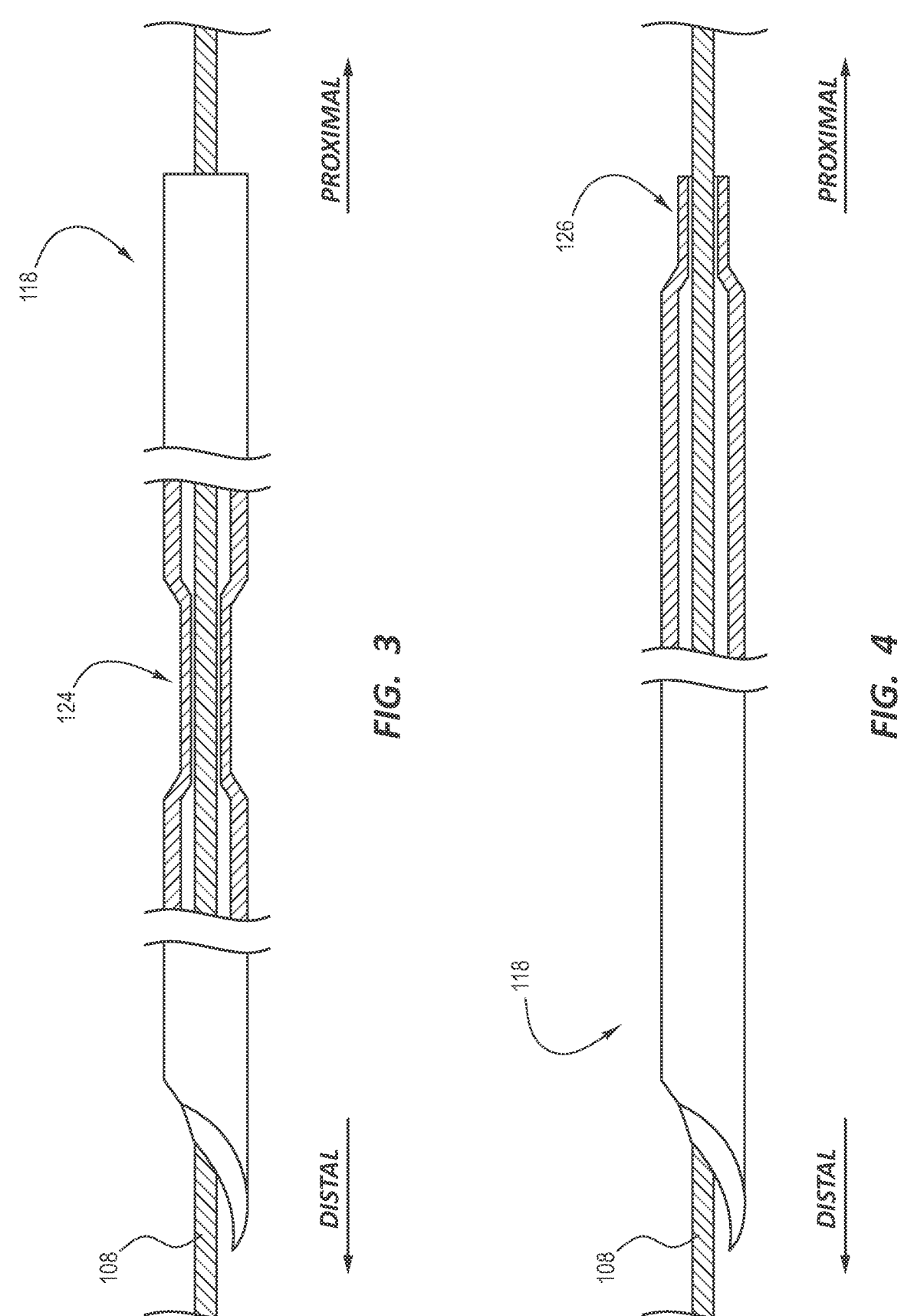
FIG. 3 illustrates a swaged or crimped section of the needle shaft in accordance with some embodiments.
FIG. 4 illustrates another swaged or crimped section of the needle shaft in accordance with some embodiments.

FIGS. 3 and 4 illustrate swaged or crimped sections of the needle shaft in accordance with some embodiments.

As shown, the blood egress-mitigating means can include a swaged or crimped section 124 or 126 in a proximal portion of the needle shaft 118. The swaged or crimped section 124 is in the proximal portion of the needle shaft 118 but distal of a proximal end of the needle shaft 118, whereas the swaged or crimped section 126 is in the proximal portion of the needle shaft 118 including the proximal end of the needle shaft 118. The swaged or crimped section 124 or 126 has a smaller outer diameter than a remainder of the needle shaft 118 unless the needle shaft 118 includes more than one swaged or crimped section such as the swaged or crimped section 124 or 126. If the needle shaft 118 includes more than one swaged or crimped section, the swaged or crimped sections have smaller outer diameters than unmodified (i.e., not swaged or crimped) sections of the needle shaft 118. The swaged or crimped section 124 or 126 has a reduced annular space. Indeed, a transverse cross section of the reduced annular space in the swaged or crimped section 124 or 126 can have a minimum annular width $w_{min}$ of about 25 μm. The reduced annular space retards blood flow therethrough, as well as through the proximal end of the needle 102.

Advantageously, when the needle shaft 118 includes the swaged or crimped section 124 or 126, the needle hub 120 can be disposed over the swaged or crimped section 124 or 126 and coupled (e.g., bonded or adhered) thereto.

Needle Modifications: Embossed Sections of the Needle Shaft

Figures 5, 6, 7:
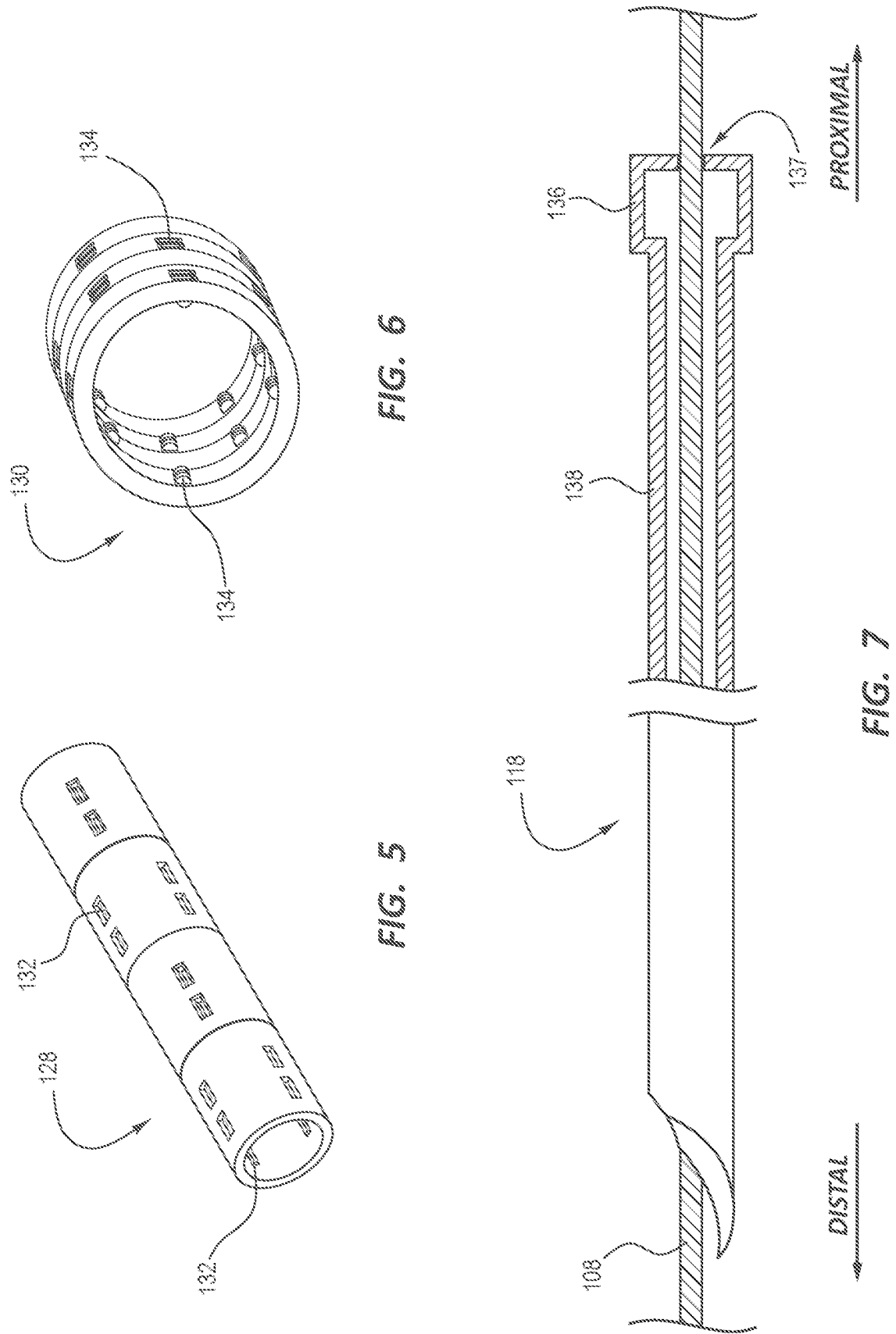
FIG. 5 illustrates an embossed section of the needle shaft in accordance with some embodiments.
FIG. 6 illustrates another embossed section of the needle shaft in accordance with some embodiments.
FIG. 7 illustrates a reservoir in the needle shaft in accordance with some embodiments.

FIGS. 5 and 6 illustrate embossed sections 128 and 130 of the needle shaft in accordance with some embodiments.

As shown, the blood egress-mitigating means can include the embossed section 128 or 130 in the proximal portion of the needle shaft 118. The embossed section 128 or 130 has a plurality of embossments 132 or 134 in an abluminal surface of the needle shaft 118 extending into the annular space 106. The plurality of embossments 132 in the embossed section 128 is a regular array of longitudinally embossed ribs, whereas the plurality of embossments 134 in the embossed section 130 is a regular array of circumferentially embossed ribs; however, the plurality of embossments 132 or 134 are not limited thereto. Indeed, the plurality of embossments 132 or 134 can instead be obliquely embossed ribs or a mixture of longitudinally embossed ribs, circumferentially embossed ribs, or obliquely embossed ribs in a regular or random array. The plurality of embossments 132 or 134 contributes to a reduced annular space and a torturous fluid path for retarding blood flow through the embossed section 128 or 130.

Needle Modifications: Reservoir

FIG. 7 illustrates a reservoir 136 in the needle shaft 118 in accordance with some embodiments.

As shown, the blood egress-mitigating means can include the reservoir 136 in the proximal portion of the needle shaft 118. In such embodiments, the reservoir 136 can include the proximal end of the needle shaft 118. The reservoir 136, in turn, includes a guidewire aperture 137 in a proximal end thereof through which the access guidewire 108 is allowed to axially move. However, the reservoir 136 can alternatively be in the proximal portion of the needle shaft 118 but distal of the proximal end of the needle shaft 118. Also, while the reservoir 136 can be integral with the needle shaft 118 (i.e., formed together with the needle shaft 118 or in a separate step of forming the needle shaft 118) as shown, the reservoir 136 can alternatively be a separately formed container disposed over the proximal end of the needle shaft 118 or even a side hole in a side wall 138 in the proximal portion the needle shaft 118. If translucent, such a container can be advantageously used for visualizing blood flashback when combined with a translucent portion of the body 112 of the device 100 through which the reservoir 136 can be seen in at least the ready-to-deploy state of the device 100. Whether the reservoir 136 includes the proximal end of the needle shaft 118 or the reservoir 136 is distal thereto, the reservoir 136 is integral with the needle shaft 118 or the reservoir 136 is formed separately from the needle shaft 118 and disposed thereover, or some combination thereof, the reservoir 136 can be disposed in the device 100 distal of a distal member 140 of the needle hub 120, securely between the distal member 140 and a proximal member 142 of the needle hub 120, or proximal of the proximal member 142. The reservoir 136 provides a space for collecting blood therein for mitigating blood egress from the device 100.

Notwithstanding the foregoing, the blood egress-mitigating means can further include a composition of a superabsorbent polymer, a cellulosic polymer (e.g., POLYOX™ by DuPont de Nemours, Inc. of Wilmington, Delaware), a coagulant, or a combination thereof disposed in the reservoir 136 for absorbing blood, coagulating blood, or a combination thereof. Optionally, the composition is a dispersion or a solution with a liquid such as water as a continuous medium or a solvent, respectively. The superabsorbent polymer dispersed or dissolved in the liquid forms a hydrogel that can either further absorb blood up to its absorbance capacity, retard blood flow through the reservoir 136 or the needle shaft 118 by occlusion thereof, or a combination thereof. With respect to retarding blood flow through the reservoir 136 or the needle shaft 118 by occlusion thereof, an oil-based lubricant (e.g., silicone oil-based lubricant) can be used as an alternative to the composition including superabsorbent polymer, a cellulosic polymer, the coagulant, or the combination thereof.

Needle Modifications: Side Wall Thickness

While not shown, the blood egress-mitigating means can include increasing a thickness of the side wall 138 of the needle shaft 118 such that an inner diameter of the needle shaft 118 is closer in diameter to an outer diameter of the access guidewire 108, an outer diameter of the needle shaft 118 is closer in diameter to an inner diameter of the catheter tube 114, or a combination thereof. Optimization of the foregoing diameters contributes to a reduced annular space for retarding blood flow therethrough.

Needle Modifications: Inserts

Figures 8, 9:
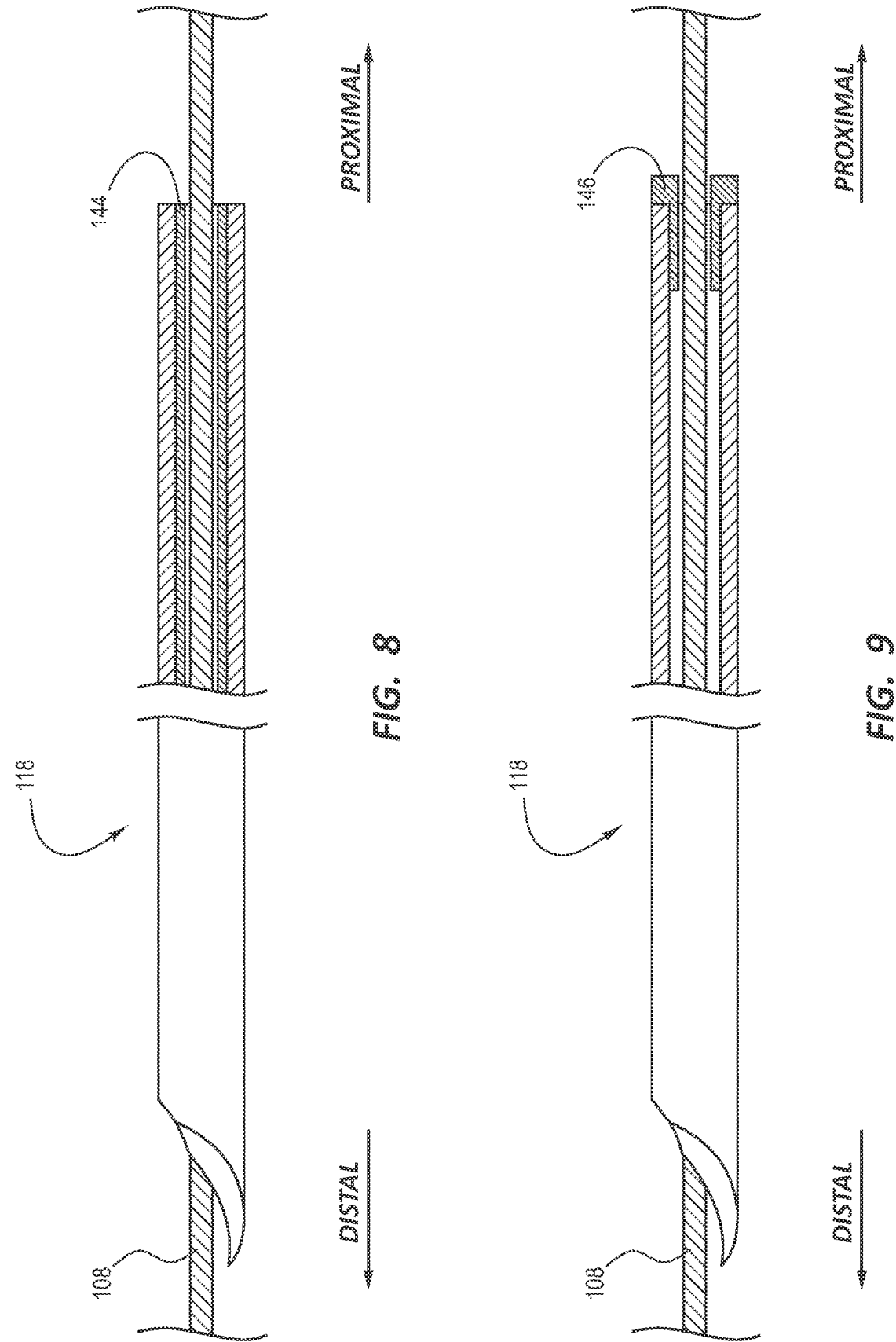
FIG. 8 illustrates a tubular insert inserted into the needle shaft in accordance with some embodiments.
FIG. 9 illustrates a holed stopper inserted into the needle shaft in accordance with some embodiments.

FIG. 8 illustrates a tubular insert 144 inserted into the needle shaft 118 in accordance with some embodiments.

As shown, the blood egress-mitigating means can include the tubular insert 144 inserted into the proximal portion of the needle shaft 118 between the needle shaft 118 and the access guidewire 108. The tubular insert 144 assumes a portion of the needle lumen, but the tubular insert 144 includes a tubular-insert lumen through which the access guidewire 108 is allowed to axially move. By assuming a portion of the needle lumen, the tubular insert 144 contributes to a reduced annular space for retarding blood flow through the needle lumen. Advantageously, the tubular insert 144 can be porous (e.g., porous polyethylene) with a porosity configured to allow air but not blood therethrough. Such a configuration of the tubular insert 144 facilitates more rapid blood flashing upon inserting the needle 102 into a blood vessel by allowing air in the needle shaft 118 to more rapidly escape through a combination of the pores of the tubular insert 144 and the portion of the tubular-insert lumen not occupied by the access guidewire 108.

FIG. 9 illustrates a holed stopper 146 inserted into needle shaft 118 in accordance with some embodiments.

As shown, the blood egress-mitigating means can include the holed stopper 146 inserted into the proximal end of the needle shaft 118. The holed stopper 146 can be formed of a solid or porous polymeric material. In addition, the holed stopper 146 can include a flanged proximal end, which, like the reservoir 136, can be disposed in the device 100 distal of the distal member 140 of the needle hub 120, securely between the distal member 140 and the proximal member 142 of the needle hub 120, or proximal of the proximal member 142. A distal portion of the holed stopper 146 assumes a portion of the needle lumen in the proximal portion of the needle shaft 118, but the holed stopper 146 includes a longitudinal through hole through which the access guidewire 108 is allowed to axially move. By assuming a portion of the needle lumen, the holed stopper 146 contributes to a reduced annular space for retarding blood flow through the needle lumen. Advantageously, the holed stopper 146 can be porous (e.g., porous polyethylene) with a porosity configured to allow air but not blood therethrough. Such a configuration of the holed stopper 146 facilitates more rapid blood flashing upon inserting the needle 102 into a blood vessel by allowing air in the needle shaft 118 to more rapidly escape through a combination of the pores of the holed stopper 146 and the portion of the longitudinal through hole not occupied by the access guidewire 108.

FIG. 10 illustrates one or more 'O'-rings 148 inserted into the needle shaft 118 in accordance with some embodiments.

As shown, the blood egress-mitigating means can include the one-or-more 'O'-rings 148 inserted into the proximal portion of the needle shaft 118 between the needle shaft 118 and the access guidewire 108. The one-or-more 'O'-rings 148 assume a portion of the needle lumen, but the one-or-more 'O'-rings 148 respectively include one or more centers through which the access guidewire 108 is allowed to axially move. By assuming a portion of the needle lumen, the one-or-more 'O'-rings 148 contribute to a reduced annular space for retarding blood flow through the needle lumen.

Needle Modifications: Attachments

FIG. 11 illustrates a conical funnel 150 coupled to the needle shaft 118 in accordance with some embodiments.

As shown, the blood egress-mitigating means can include the conical funnel 150 formed of a polymeric material. The conical funnel 150 includes a mouth coupled (e.g., bonded or adhered) to the proximal end of the needle shaft 118 and a tapered portion that proximally tapers onto the access guidewire 108. Optionally, the conical funnel 150 includes a neck proximally extending over the access guidewire 108 from the tapered portion. Whether or not the conical funnel 150 includes the neck, the conical funnel 150 retards blood flow through a proximal opening of the conical funnel 150, which retards blood flow through the needle lumen.

Needle Hub Modifications

Figure 12:
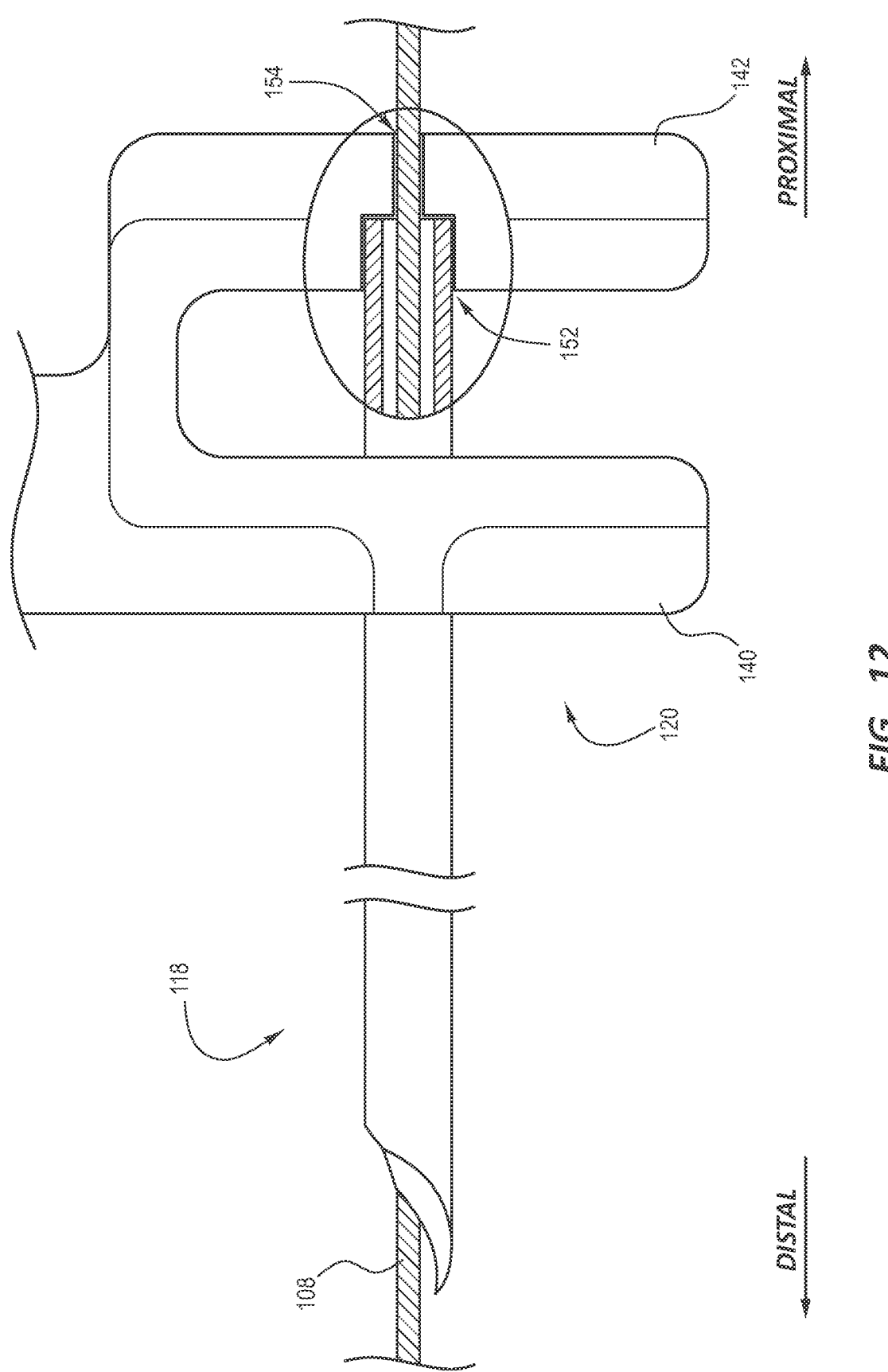
FIG. 12 illustrates the needle shaft disposed in a bore of the needle hub in accordance with some embodiments.

FIG. 12 illustrates the needle shaft 118 disposed in a bore 152 of the needle hub 120 in accordance with some embodiments.

As shown, he blood egress-mitigating means can include the bore 152 through a distal face of the proximal member 142 of the needle hub 120 having a through hole 154 dimensioned such that only the access guidewire 108 is allowed therethrough. By allowing only the access guidewire 108 through the through hole 154, the through hole 154 contributes to a reduced annular space with a minimum annular width $w_{min}$ of about 25 μm for retarding blood flow through the proximal end of the needle shaft 118.

Composition-Based Modifications for the Needle Shaft

Figures 13, 14:
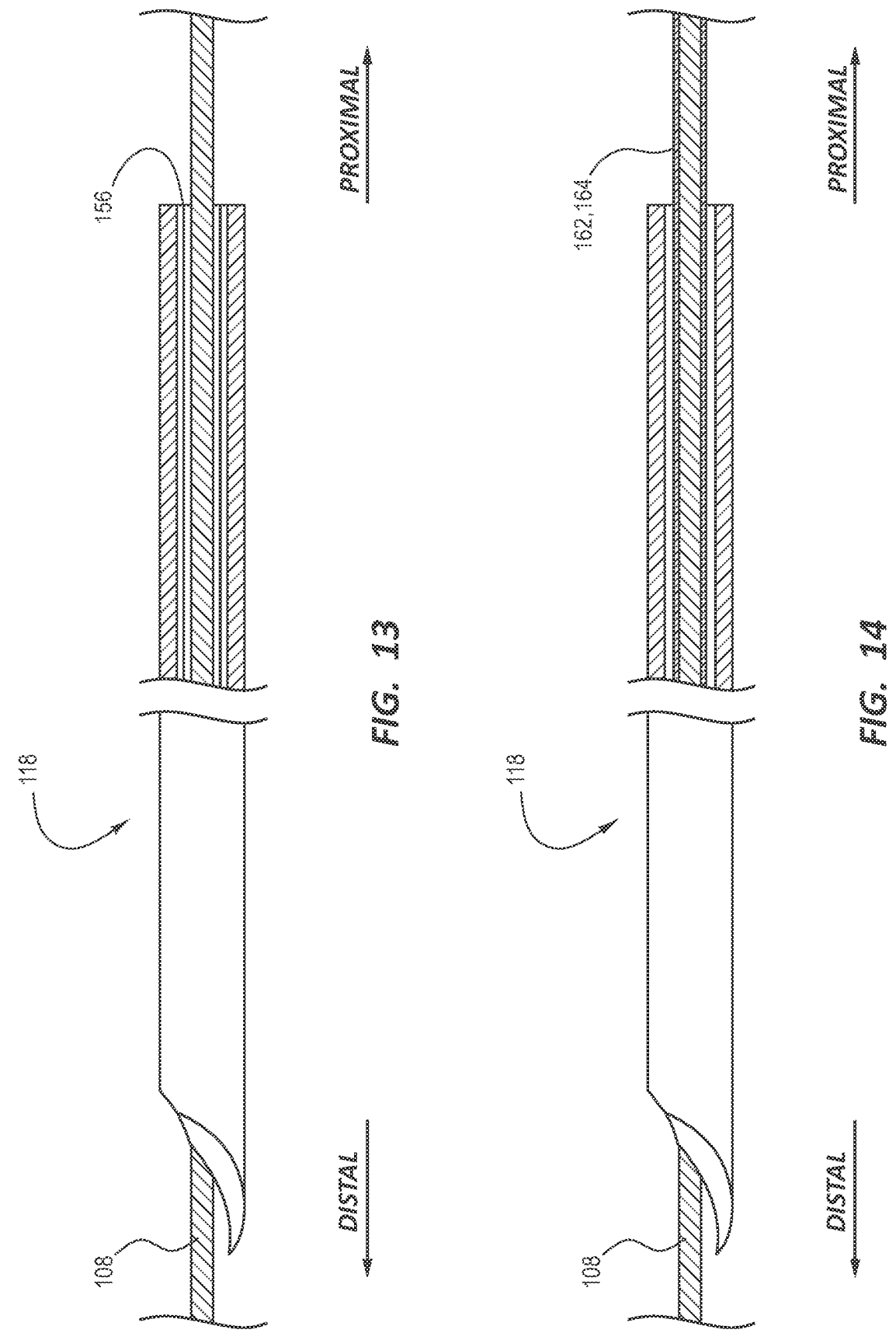
FIG. 13 illustrates a coating on the luminal surface of the needle shaft in accordance with some embodiments.
FIG. 14 illustrates a coating on the surface of the access guidewire in accordance with some embodiments.

FIG. 13 illustrates a coating 156 on the luminal surface of the needle shaft 118 in accordance with some embodiments.

As shown, the blood egress-mitigating means can include a composition disposed in the proximal portion of the needle lumen such as the coating 156 on the luminal surface of the needle shaft 118 up to the proximal end thereof. The composition or the coating 156 thereof can include a superabsorbent polymer, a cellulosic polymer (e.g., POLYOX™ by DuPont de Nemours, Inc. of Wilmington, Delaware), a coagulant, or a combination thereof for absorbing blood, coagulating blood, or a combination thereof. Optionally, the composition is a dispersion or a solution with a liquid such as water as a continuous medium or a solvent, respectively. The superabsorbent polymer dispersed or dissolved in the liquid forms a hydrogel that can either further absorb blood up to its absorbance capacity, retard blood flow through the needle shaft 118 by occlusion thereof, or a combination thereof.

Figures 15, 16:
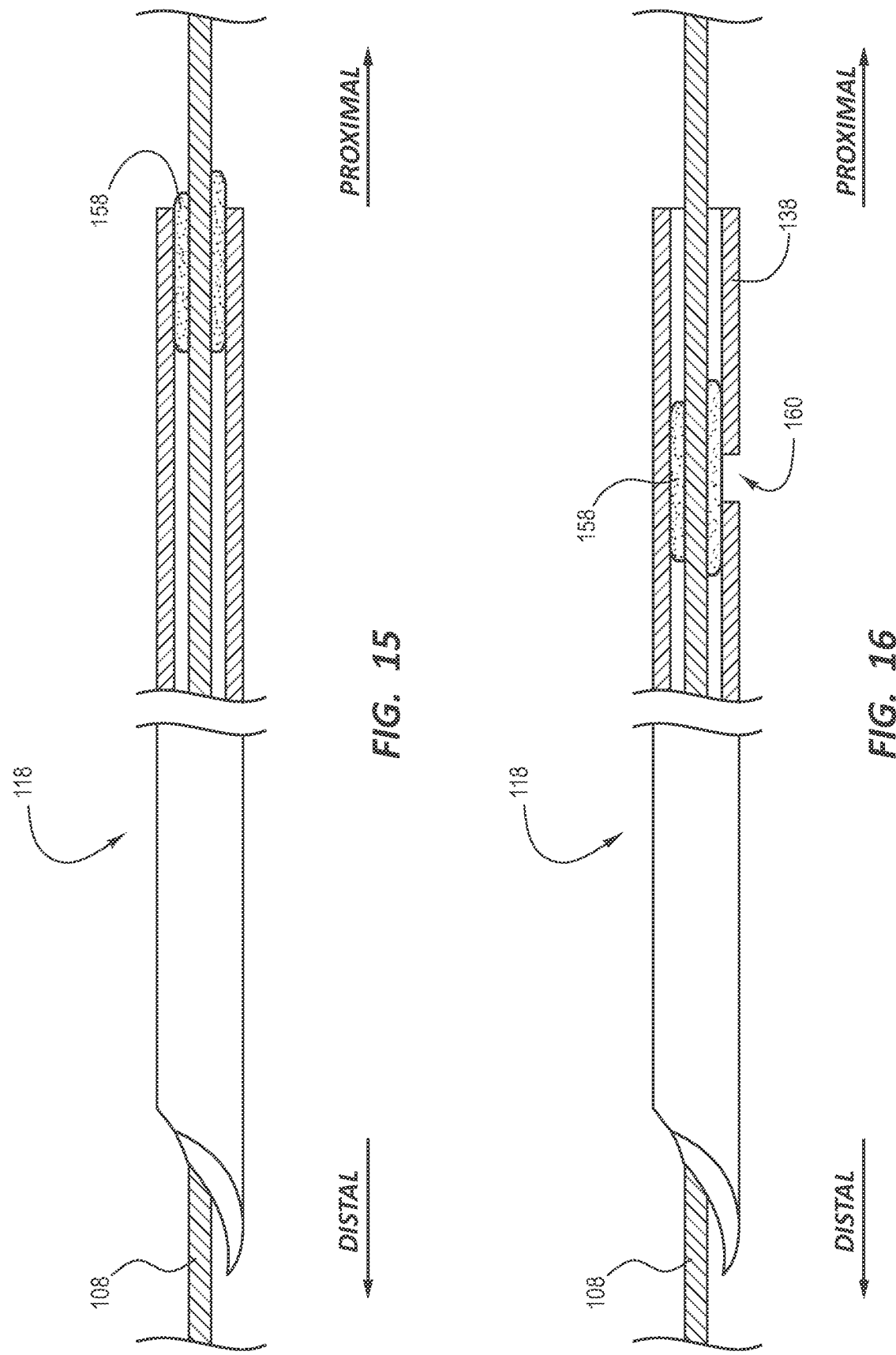
FIG. 15 illustrates a lubricant disposed in the needle shaft in accordance with some embodiments.
FIG. 16 illustrates the lubricant disposed in the needle shaft having a cutout therefor in accordance with some embodiments.

FIGS. 15 and 16 illustrate a lubricant disposed in the needle shaft in accordance with some embodiments.

As shown, the blood egress-mitigating means can include an amount of a lubricant 158 such as an oil-based lubricant (e.g., silicone oil-based lubricant) disposed in the needle lumen in the proximal portion of the needle shaft 118. While the lubricant 158 can be injected into the needle lumen through the proximal end of the needle shaft 118, the needle shaft 118 can alternatively include a cutout 160 through the side wall 138 in the proximal portion of the needle shaft 118 configured for injecting the lubricant 158 into the needle lumen. The lubricant 158 occludes the needle lumen, which retards or blocks blood flow through the proximal end of the needle shaft 118.

Advantageously, the lubricant 158 in the needle lumen also lubricates the access guidewire 108, thereby facilitating axial movement of the access guidewire within the needle lumen.

Composition-Based Modifications for the Access Guidewire

FIG. 14 illustrates a coating 162 on the surface of the access guidewire 108 in accordance with some embodiments.

As shown, the blood egress-mitigating means can include a composition disposed on the surface of the access guidewire 108 such as the coating 162 on at least a portion of the access guidewire 108 commensurate with the proximal portion of the needle shaft 118 in the ready-to-deploy state of the device 100. The composition or the coating 162 thereof can include a superabsorbent polymer, a cellulosic polymer (e.g., POLYOX™ by DuPont de Nemours, Inc. of Wilmington, Delaware), a coagulant, or a combination thereof for absorbing blood, coagulating blood, or a combination thereof. Optionally, the composition is a dispersion or a solution with a liquid such as water as a continuous medium or a solvent, respectively. The superabsorbent polymer dispersed or dissolved in the liquid forms a hydrogel that can either further absorb blood up to its absorbance capacity, retard blood flow through the needle shaft 118 by occlusion thereof, or a combination thereof.

Alternatively, the composition disposed on the surface of the access guidewire 108 is a polymeric coating 164 over at least the portion of the access guidewire 108 commensurate with the proximal portion of the needle shaft 118 in the ready-to-deploy state of the device 100. The polymeric coating 164 bulks up the access guidewire 108 such that the polymeric coating 164 assumes a portion of the needle lumen of the proximal portion of the needle shaft 118. By assuming a portion of the needle lumen, the polymeric coating 164 contributes to a reduced annular space for retarding blood flow through the needle lumen.

It should be understood, the blood egress-mitigating means is not limited to any one of the foregoing means for mitigating blood egress. Indeed, combinations of the blood egress-mitigating means set forth above are also useful.

Methods

Methods include at least a method of using the integrated catheter-placement device 100. Such a method can include an obtaining step, a needle tract-establishing step, an access guidewire-advancing step, a catheter-advancing step, and a withdrawing step.

The obtaining step includes obtaining the device 100. As set forth above, the device includes the needle 102 including the needle shaft 118 disposed in the catheter tube 114 of the intravascular catheter 110 in at least the ready-to-deploy state of the device 100.

The needle tract-establishing step includes establishing a needle tract from an area of skin to a blood-vessel lumen of a patient with the needle 102. The needle tract-establishing step causes blood to flash back into the device 100 but without egressing from the device 100 in accordance with one or more blood egress-mitigating means set forth above for mitigating blood egress from the device 100.

The access guidewire-advancing step includes advancing the access guidewire 108 disposed in the needle lumen of the needle 102 into the blood-vessel lumen.

The catheter-advancing step includes advancing the catheter tube 114 over the needle 102 and into the blood-vessel lumen.

The withdrawing step includes withdrawing both the needle 102 and the access guidewire 108 from the blood-vessel lumen leaving the catheter 110 behind with the catheter tube 114 disposed in the blood-vessel lumen of the patient.

As set forth above, the blood egress-mitigating means can reduce or block the annular space within the needle shaft 118 defined by the luminal surface of the needle shaft 118 and the surface of the access guidewire 108 for retarding or blocking blood flow therethrough. Additionally or alternatively, the blood egress-mitigating means can include the reservoir 136 or the like fluidly coupled to the needle lumen for collecting blood therein. Additionally or alternatively, the blood egress-mitigating means can include the composition including the superabsorbent polymer, the cellulosic polymer, the coagulant, or the combination thereof for absorbing or coagulating blood therewith.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. An integrated catheter-placement device, comprising:
an intravascular catheter including a catheter tube and catheter hub, the intravascular catheter extending from a body of the integrated catheter-placement device in at least a ready-to-deploy state of the integrated catheter-placement device;
a needle including a needle shaft and a needle hub, the needle shaft extending through the catheter tube by way of a catheter-tube lumen thereof in at least the ready-to-deploy state of the integrated catheter-placement device;
an access guidewire disposed in a needle lumen of the needle; and
a blood egress-mitigating means for mitigating blood egress from an annular space within the needle shaft defined by a luminal surface of the needle shaft and a surface of the access guidewire while still allowing the access guidewire to axially move within the needle lumen, the blood egress-mitigating means including a reservoir integral with a proximal portion of the needle shaft, the reservoir providing a space for collecting blood.

2. The device of claim 1, wherein the proximal portion of the needle shaft terminates with the reservoir.

3. The device of claim 2, wherein the reservoir includes a guidewire aperture in a proximal end thereof through which the access guidewire is allowed to axially move.

4. The device of claim 3, wherein the blood egress-mitigating means further includes a composition including a superabsorbent polymer, a cellulosic polymer, a coagulant, or a combination thereof disposed in the reservoir for absorbing or coagulating blood therewith.

5. The device of claim 2, wherein the blood egress-mitigating means further includes a composition including a superabsorbent polymer, a cellulosic polymer, a coagulant, or a combination thereof disposed in the reservoir for absorbing or coagulating blood therewith.

6. The device of claim 1, wherein the blood egress-mitigating means includes an amount of an oil-based lubricant disposed in the needle lumen in the proximal portion of the needle shaft, the oil-based lubricant blocking or retarding blood flow through a proximal end of the needle shaft.

7. The device of claim 6, wherein the needle shaft includes a cutout through a needle-shaft wall in the proximal portion of the needle shaft, the cutout configured for injecting the oil-based lubricant into the needle lumen.

8. The device of claim 1, wherein the reservoir includes a guidewire aperture in a proximal end thereof through which the access guidewire is allowed to axially move.

9. The device of claim 1, wherein the blood egress-mitigating means further includes a composition including a superabsorbent polymer, a cellulosic polymer, a coagulant, or a combination thereof disposed in the reservoir for absorbing or coagulating blood therewith.

10. The device of claim 1, wherein the blood egress-mitigating means includes a polymeric coating over the surface of the access guidewire, the polymeric coating assuming a portion of the needle lumen, thusly contributing to a reduced annular space for retarding blood flow there-through.

11. A method of an integrated catheter-placement device, comprising:
  obtaining the integrated catheter-placement device, the integrated catheter-placement device including:
    an intravascular catheter including a catheter tube and catheter hub, the intravascular catheter extending from a body of the integrated catheter-placement device in at least a ready-to-deploy state of the integrated catheter-placement device; and
    a needle including a needle shaft and a needle hub, the needle shaft extending through the catheter tube by way of a catheter-tube lumen thereof in at least the ready-to-deploy state of the integrated catheter-placement device;
  establishing a needle tract from an area of skin to a blood-vessel lumen of a patient with the needle, the establishing of the needle tract causing blood to flash back into the integrated catheter-placement device without egressing from an annular space within the needle shaft defined by a luminal surface of the needle shaft and a surface of an access guidewire in accordance with a blood egress-mitigating means for mitigating blood egress therefrom, the blood egress-mitigating means including a reservoir integral with a proximal portion of the needle shaft that provides a space for collecting blood;

advancing the access guidewire disposed in a needle lumen of the needle into the blood-vessel lumen;
  advancing the catheter tube over the needle and into the blood-vessel lumen; and
  withdrawing both the needle and the access guidewire from the blood-vessel lumen leaving the intravascular catheter behind with the catheter tube disposed in the blood-vessel lumen of the patient.

12. The method of claim 11, wherein the blood egress-mitigating means further includes a composition including a superabsorbent polymer, a cellulosic polymer, a coagulant, or a combination thereof disposed in the reservoir for absorbing or coagulating blood therewith.

13. The method of claim 12, wherein the reservoir includes a guidewire aperture in a proximal end thereof through which the access guidewire is allowed to axially move.

14. The method of claim 13, wherein the proximal portion of the needle shaft terminates with the reservoir.

15. The method of claim 11, wherein the reservoir includes a guidewire aperture in a proximal end thereof through which the access guidewire is allowed to axially move.

16. The method of claim 11, wherein the proximal portion of the needle shaft terminates with the reservoir.

17. The method of claim 12, wherein the proximal portion of the needle shaft terminates with the reservoir.

* * * * *